US008227012B2

(12) United States Patent  
DeLine et al.

(10) Patent No.: US 8,227,012 B2
(45) Date of Patent: Jul. 24, 2012

(54) GRAIN FRACTION EXTRACTION MATERIAL PRODUCTION SYSTEM

(75) Inventors: Kenneth E. DeLine, Avon, CO (US); Daniel L. Claycamp, West Frankfort, IL (US); Daniel Fetherston, Cape Girardeau, MO (US); Rodger T. Marentis, Macungie, PA (US)

(73) Assignee: MOR Technology, LLC, Metropolis, IL (US)

( * ) Notice: Subject to any disclaimer, the term of this patent is extended or adjusted under 35 U.S.C. 154(b) by 857 days.

(21) Appl. No.: 12/001,624

(22) Filed: Dec. 12, 2007

(65) Prior Publication Data

US 2008/0233253 A1  Sep. 25, 2008

Related U.S. Application Data (63) Continuation-in-part of application No. 11/726,255, filed on Mar. 21, 2007, now Pat. No. 7,524,522.

(60) Provisional application No. 60/838,642, filed on Aug. 18, 2006.

(51) Int. Cl.
A23L 1/025 (2006.01)
A23L 1/10 (2006.01)
(52) U.S. Cl. ........... 426/622; 426/11; 426/18; 426/330; 426/312; 426/429; 426/430; 426/442; 426/483; 426/518; 426/661
(58) Field of Classification Search .......... 426/622, 426/661, 518, 429, 442, 330.43, 312, 11, 426/18, 483
See application file for complete search history.

(56) References Cited

U.S. PATENT DOCUMENTS

| | | |
|---|---|---|
| 4,018,755 A | 4/1977 | Wang |
| 4,059,604 A | 11/1977 | Kresse |
| 4,083,836 A | 4/1978 | Anjou et al. |
| 4,325,882 A | 4/1982 | Reiners |
| 4,341,713 A | 7/1982 | Stolp et al. |
| 446,692 A | 8/1984 | Friedrich |
| 4,495,207 A | 1/1985 | Christianson et al. |
| 4,515,726 A | 5/1985 | Sullivan |
| 4,576,820 A | 3/1986 | Hussmann |
| 467,513 A | 6/1987 | Eggers et al. |
| 474,492 A | 5/1988 | Rice |
| 4,859,371 A | 8/1989 | Diosady et al. |
| 4,898,673 A | 2/1990 | Rice et al. |
| 4,994,272 A | 2/1991 | Hussmann |

(Continued)

FOREIGN PATENT DOCUMENTS

CN 1242416 1/2000

(Continued)

OTHER PUBLICATIONS

Hubbar, J. D. et al. Lipid Extraction from Wheat Flour Using Supercritical Fluid Extraction, Jun. 10, 2004, Cereal Chem. 81(6):693-698.*

(Continued)

*Primary Examiner* — Helen F Heggestad
(74) *Attorney, Agent, or Firm* — Craig R. Miles; CR Miles, P.C.

(57) ABSTRACT

Specifically, a dry corn fractionation system which operates to produce an endosperm fraction which can be concurrently of greater purity at greater yield than obtainable from corn milling or dry corn milling processes.

12 Claims, 9 Drawing Sheets

U.S. PATENT DOCUMENTS

| | | | |
|---|---|---|---|
| 512,055 | A | 6/1992 | Nguyen et al. |
| 5,138,075 | A | 8/1992 | Ohgaki et al. |
| 5,250,313 | A | 10/1993 | Giguere |
| 5,252,729 | A | 10/1993 | De Crosta et al. |
| 5,295,629 | A | 3/1994 | Satake et al. |
| 5,498,384 | A | 3/1996 | Volk et al. |
| 5,680,812 | A | 10/1997 | Linsgeseder |
| 5,685,218 | A | 11/1997 | Kemper |
| 5,759,549 | A | 6/1998 | Hiltunen et al. |
| 5,826,500 | A | 10/1998 | Kemper |
| 593,210 | A | 8/1999 | Kanel et al. |
| 5,997,877 | A | 12/1999 | Chang |
| 6,201,142 | B1 | 3/2001 | Maza |
| 6,254,914 | B1 | 7/2001 | Singh et al. |
| 6,326,035 | B1 | 12/2001 | Nakatani et al. |
| 6,368,649 | B1 | 4/2002 | van Bommel |
| 6,398,036 | B1 | 6/2002 | Griebat et al. |
| 6,495,175 | B2 | 12/2002 | Rao et al. |
| 6,504,085 | B1 | 1/2003 | Howard |
| 6,570,030 | B2 | 5/2003 | Goto et al. |
| 6,664,405 | B2 | 12/2003 | Lee |
| 6,814,998 | B1 | 11/2004 | Ozawa et al. |
| 6,899,910 | B2 | 5/2005 | Johnston et al. |
| 6,936,110 | B2 | 8/2005 | Van Thorre |
| 6,936,294 | B2 | 8/2005 | Matthews et al. |
| 6,953,165 | B1 | 10/2005 | Griebat et al. |
| 7,037,548 | B2 | 5/2006 | Ozawa et al. |
| 7,074,449 | B1 | 7/2006 | Holley et al. |
| 7,087,720 | B2 | 8/2006 | Murray et al. |
| 7,138,257 | B2 | 11/2006 | Galli et al. |
| 2003/0019736 | A1 | 1/2003 | Garman |
| 2004/0234649 | A1 | 11/2004 | Lewis et al. |
| 2005/0233030 | A1 | 10/2005 | Lewis et al. |
| 2005/0239181 | A1 | 10/2005 | Lewis et al. |
| 2006/0035354 | A1 | 2/2006 | Galli et al. |
| 2007/0037267 | A1 | 2/2007 | Lewis et al. |

FOREIGN PATENT DOCUMENTS

| | | |
|---|---|---|
| CN | 1522596 | 8/2004 |
| GB | 366516 | 1/1932 |
| GB | 707385 | 4/1954 |
| GB | 1058076 | 2/1967 |
| GB | 1398459 | 6/1975 |
| JP | 6136384 | 5/1994 |
| JP | 6299187 | 10/1994 |
| MX | PA99000033 | 9/2004 |

OTHER PUBLICATIONS

U.S. Appl. No. 60/838,642, filed Aug. 18, 2006 entitled "Kernel Fractionation Process".

Kleber, Mark, Mississippi Renewable Energy Conference—Mar. 25-26, 2003, mg engineering Lurgi PSI, Biodesel Capabilities, 2003, pp. 1-28.

Holcomb, et al. SFE Extraction of alfatoxins (B1, B2, G1, and G2) from corn and analysis by HPLC. The Journal of Supercritical Fluids, vol. 9 Issue 2, Jun. 1996, pp. 118-121.

Ronyai, E., et al. Supercritical fluid extraction of corn germ with carbon dioxide-ethyl alcohol mixture. The Journal of Supercritical Fluids, vol. 14,1, Oct. 1998, pp. 75-81.

Otles, Semih. Supercritical Fluids and Its Applications in Food Industry. http://eng.ege.edu.tr/~otles/SupercriticalFluids-ScienceAndTechnology/bolumb/Wc197588f62dd7.htm, Mar. 19, 2007.

Taylor, Scott L., et al., Determination of Oil Content in Oilseeds by Analytical Supercritical Fluid Extraction, JAOCS, vol. 70 Issue 4, Apr. 1993, pp. 437-439.

Kice Industries, Inc. web site, Multi-Aspirators, http://www.kice.com/products/multiaspirators/index.html, Mar. 19, 2007, seven total pages.

Kice Industries, Inc. web site, Bran Finisher, http://www.kice.com/products/branfinisher/index.html, Mar. 19, 2007, three total pages.

GBS Group, BI-MIX Intensive Dampener product brochure, Sangati Berga, Golfetto, Jun. 2002, three total pages.

GBS Group, Synthesis Rollermill product brochure, Sangati Berga, Golfetto, Jun. 2002, fourteen total pages.

Satake Corporation web site, Maize Degermer VBF product page and brochure, http:/www.satake.co.uk, Mar. 21, 2007, two total pages.

Forsbergs, Inc. web site, cutomer satisfaction page, P-Series Destoners product page, and Vacuum Gravityy Separator, http:/www.forsbergs,com, Mar. 21, 2007, seven total pages.

Great Western Manufacturing web site, "HS" Free Swinging Sifter product brochure, http:/www.gwmfg.com, Mar. 19, 2007, five total pages.

E. Reverchon, G. Della Porta, D. Gorgoglione. Supercritical $CO_2$ fractionation of jasmine concrete. J. Supercrit. Fluids 8 (1995) 60-65.

E. Reverchon, G. Della Porta. Rose concrete fractionation by supercritical $CO_2$. J. Supercrit. Fluids 9 (1996) 199-204.

R. L. Smith Jr., et al., Separation of cashew (*Anacardium occidentale* L.) nut shell liquid with supercritical carbon dioxide. Biores. Technol. 88 (2003) 1-7.

M. A. Rostagno, J.M.A. Araujo, D. Sandi. Supercritical fluid extraction of isoflavones from soybean flour, Food Chem. 78 (2002) 111-117.

L. Sesti Osseo, G. Caputo, I. Gracia, E. Reverchon. Continuous fraction of used frying oil by supercritical $CO_2$. J. Am. Oil Chem. Soc. (JAOCS) 81 (9) (2004) 879-885.

Alberto Bertucco, et al., Simulated moving bed technology for continuous, countercurrent solid-fluid . . . , The Journal of Supercritical Fluids, vol. 8, 2, Jun. 1995, pp. 138-148.

H. Lee, B.H. Chung and Y. Park. Concentration of tocopherols from soybean sludge by supercritical carbon dioxide. JAOCS 68 (1991), p. 571.

G. Brunner, et al., Separation of tocopherols from deodorizer condensates by countercurrent extraction with carbon dioxide. J. Supercrit. Fluids 4 (1991), p. 72.

G. Brunner. Gas Extraction—An Introduction to Fundamentals of Supercritical Fluid and the Application to Separation Processes. Springer, Berlin (1994).

J.A. Briones, J.C. Mullins and M.G. Thies. Solvent extraction of fatty acids from natural oils with liquid water at elevated temperatures and pressures. JAOCS 67 (1990), p. 852.

P. Bondioli, C. Mariani, A. Lanzani, E. Fedeli and A. Muller. Squalene recovery from olive oil deodorizer distillates. JAOCS 70 (1993), p. 763.

O.J. Catchpole and J.C. von Kamp. Extraction of squalene from shark liver oil in a packed column using supercritical $CO_2$. Ind. Eng. Chem. Res. 36 (1997), p. 4318.

M.F. Mendes, et al.,Recovery of the high aggregated compounds present in the deodorizer distillate of vegetable oils using supercritical fluids. JAOCS 34:2, Jun. 2005, pp. 157-162.

D. D. Christianson, et al., Supercritical Fluid Extraction of Dry-Milled Corn Germ with Carbon Dioxide. Journal of Food Science 49 (1), 229-232, Jan. 19, 1984.

B.M.C. Soares, F.M.C. Gamarra, L.C. Paviani, L.A.G. Goncalves, F.A. Cabral. Solubility of triacyclglycerols in supercritical carbon dioxide. J. Supercrit. Fluids. 2007, 6 pp.

Ozlem Guclu-Ustundag, Feral Temelli. Correlating the solubility behavior of minor lipid components in supercritical carbon dioxide. J. of Supercritical Fluids 31 (2004) 235.

Helena Sovova, et al., Solubility of two vegetable oils in supercritical carbon dioxide. J. of Supercritical Fluids 20 (2001) pp. 15-28.

Masturah Markom, Harcharan Singh, and Masitah Hasan. Supercritical $CO_2$ fractionation of crude palm oil. J. of Supercritical Fluids 20 (2001) pp. 45-53.

U.S. Appl. No. 60/858,107, filed Nov. 10, 2006 entitled "Power Production Using Grain Fractionation Products".

U.S. Appl. No. 11/726,255, filed Mar. 21, 2007 entitled "Kernel Fractionation System".

\* cited by examiner

GRAIN FRACTION EXTRACTION MATERIAL PRODUCTION SYSTEM

This United States continuation-in-part patent application claims priority to U.S. patent application Ser. No. 11/726,255, filed Mar. 21, 2007, which claims the benefit of Provisional Patent Application No. 60/838,642, filed Aug. 18, 2006, each hereby incorporated by reference herein.

I. BACKGROUND

Specifically, a dry corn fractionation system which operates to produce an endosperm fraction which can be concurrently of greater purity at greater yield than obtainable from corn milling or dry corn milling processes.

Figure 1:
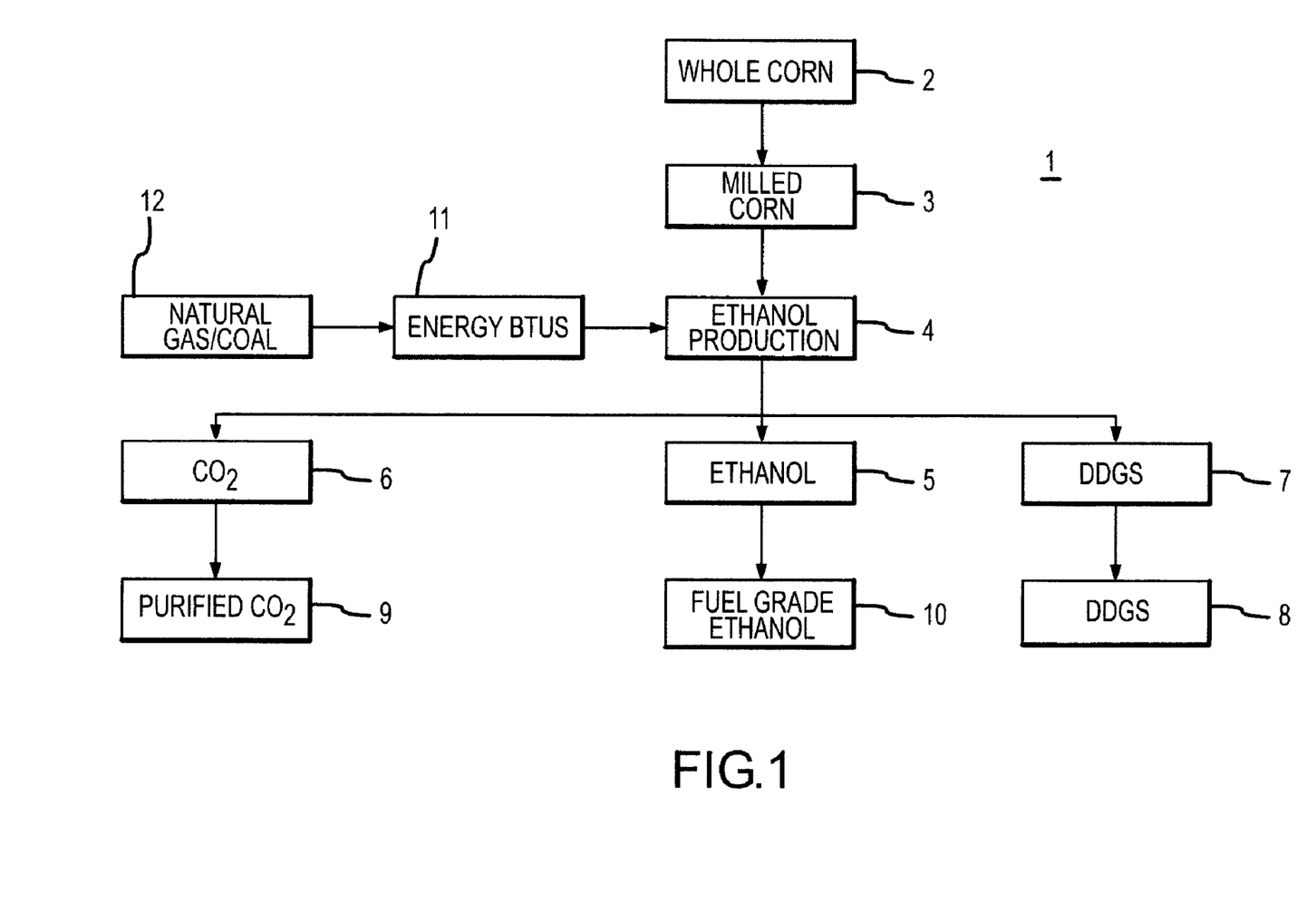
FIG. 1 is a block flow diagram of a conventional corn mill process which generates milled corn coupled to a ethanol production process.

As shown in FIG. 1, certain conventional corn mill processes for ethanol production (1) may mill an amount of whole corn (2) into a mixture of corn particles (3) (referred to hereinafter as "milled corn") which may include particles of corn bran, corn endosperm and corn germ. The milled corn (3) can be transferred to an ethanol production process (4) which includes the conventional steps of fermentation, distillation, and dehydration to generate an amount of ethanol (5). In the fermentation step, the milled corn (3) may be combined with an amount of water and an amount of alpha-amylase (or other enzyme capable of liquefying corn starch) to generate a mash in which the starch of the corn endosperm is liquefied. The mash may be held for a period of time at a temperature of between about 120 degrees Celsius (° C.) and about 150° C. to kill bacteria in the mash. The mash may then be held at a temperature of between about 90° C. and about 100° C. for a duration of time sufficient to achieve a desired level of liquefaction of the starch. An amount of gluco-amylase (or other enzyme capable of generating fermentable sugars from the liquefied starch) added to the mash converts the liquefied starch to fermentable sugars, such as dextrose, in a process referred to as saccharification. Yeast can then be added to the mash to convert the sugars to an amount of ethanol (5) and an amount of carbon dioxide (6) (or CO2) along with other volatile organics. The amount of carbon dioxide (6) can be stored or sold in the marketplace. For sale in to certain markets or for certain applications, the amount of carbon dioxide (6) can be stripped of the other volatile organics and captured as an amount of purified carbon dioxide (9). The fermented mash often referred to as "beer" comprises an amount of ethanol (5) in a concentration of about eight percent to about twenty percent by weight, other liquids and non-fermentable solids. The amount of ethanol (5) in the beer can be separated and concentrated to about 190 proof by conventional distillation techniques and dehydrated by application to molecular sieve to produce a dehydrated ethanol of about 200 proof. The about 200 proof ethanol may be combined with up to about five percent denaturant to generate an amount of fuel ethanol (10).

The stillage which remains after distillation of the beer can comprise an amount of liquid typically referred to as "thin stillage" and an amount of remaining solids typically referred to as the "distillers grains". The thin stillage can be separated from the distillers grains (for example by centrifugation). The distillers grains can be dried by evaporation of the remaining thin stillage to produce "dried distillers grains" ("DDG") (7). The thin stillage can be concentrated by evaporation of water to generate a syrup containing about thirty percent solids (also referred to as "condensed distiller soluble"). The syrup can be recombined with the dried distillers grains to generate an amount of distillers dried grain with solubles (8) ("DDGS"). The DDGS can be sold as animal feed.

Even though there is an increasing demand for fuel ethanol (10) worldwide and an increasing amount of research in ethanol production, there remain substantial unresolved problems with respect to conventional ethanol production.

A first substantial problem with conventional corn mill processes for ethanol production (1) can be that milled corn (3) introduced into the ethanol production process (4) which includes particles of corn bran, corn endosperm and corn germ requires an amount of thermal energy (11) (or energy Btus or Btus) to complete the steps of fermentation, distillation and dehydration, and by-product handling. To generate about a gallon of fuel ethanol (5), and a corresponding amount of DDGS (7) and carbon dioxide (6) the ethanol production process (4) utilizing milled corn (3) consumes an amount of thermal energy (11) of between about 30,000 and about 40,000 British thermal units (hereinafter "Btu") (the term "about" as used herein means greater or lesser than the value or range of values stated by 10 percent, but not does not limit any value or range of values to this broader definition and each value or range of values preceded by the term "about" also includes in the alternative the stated absolute value or range of values). This amount of thermal energy (11) is typically generated by burning a corresponding amount of fossil fuel (12) such as oil, coal oil, coal or natural gas. Specifically, inclusion of an amount of non-fermentable biomass or biomass largely non-fermentable, such as corn bran or corn germ, into the ethanol production process requires allocation of an amount of thermal energy (11) to process the amount of non-fermentable biomass; however, this amount of non-fermentable biomass or biomass largely non-fermentable does not produce any or produces very little ethanol which increases the amount of thermal energy (11) per unit of ethanol (5) produced as compared to an ethanol production process in which only the fermentable corn endosperm is processed. Because the corn bran and corn germ represent about 15 percent by weight of the milled corn, if the corn bran and the corn germ can be removed from the ethanol production process, than the amount of thermal energy (11) consumed by the ethanol production process (4) could be substantially reduced.

A second substantial problem with the conventional corn mill process (1) for ethanol production can be that milled corn (3) introduced into the ethanol production process (4) which includes non-fermentable biomass or biomass largely non-fermentable requires allocation an amount of fermenter capacity to biomass which does not produce any or produces very little ethanol. If the corn bran and the corn germ can be removed from the ethanol production process, then the corresponding amount of fermenter capacity freed up could be utilized to process additional fermentable biomass.

A third substantial problem with the conventional corn mill process (1) for ethanol production can be that milled corn (3) introduced into the ethanol production process (4) which includes non-fermentable biomass or biomass largely non-fermentable increases the amount of "distillers grains" produced per unit of ethanol (5) produced. The distillers grains must be dried as above-described to produce dried distiller grains ("DDG") (7) or dried distillers grains with solubles ("DDGS") (8). The drying of "distillers grains" can be the single largest point of energy consumption in the ethanol production process (4). If the corn bran and the corn germ can be removed from the ethanol production process (5), then a corresponding reduction in the amount "distillers grains" can be achieved with a corresponding reduction in the amount of thermal energy (11) utilized to produce DDG per unit of ethanol (5) produced.

A fourth substantial problem with conventional corn mill processes for ethanol production can be that the market for conventional DDG (7) by products may become saturated as the number of ethanol production facilities increases. Conventional DDG (7) includes corn bran as the amount of corn bran is increased in the DDG (7) the percent protein by weight decreases. As the percent protein by weight of the DDG (7) decreases the value of the DDG (7) or DDGS (8) as a feed. Additionally, inclusion of corn bran in the DDG increase the fat content of the DDG which can make the DDG unacceptable as a feed for poultry and fish.

Figure 2:
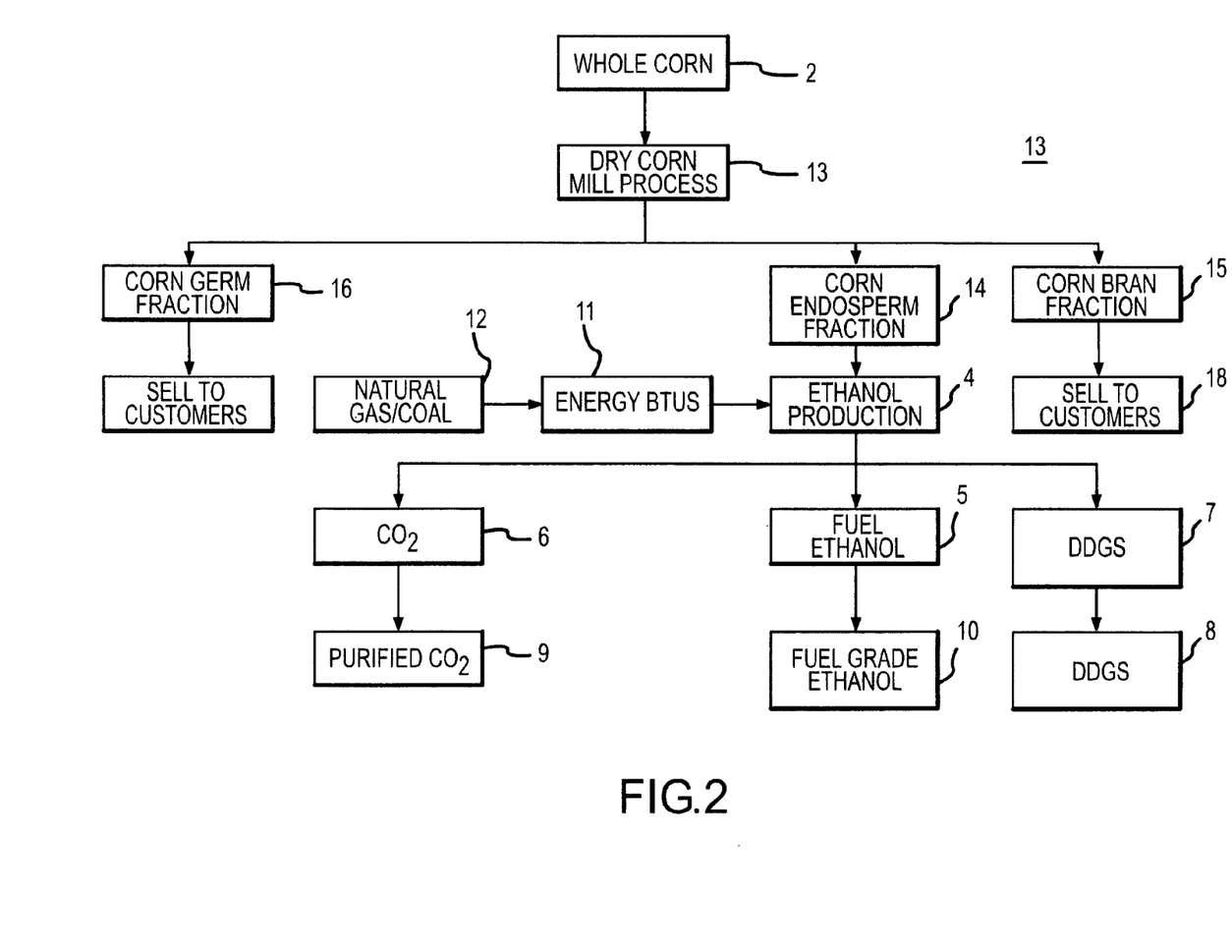
FIG. 2 is a block flow diagram of a dry corn mill process which generates corn fractions coupled to a ethanol production process.

Now referring primarily to FIG. 2, an alternative to conventional corn mill processes (1) can be a dry corn mill process (13) which facilitates isolation of a corn bran fraction (15), a corn germ fraction (16), and a corn endosperm fraction (14). The corn endosperm fraction (14) generated from the conventional dry corn mill process (13) can be introduced into an ethanol production process (4) above-described to in part address certain of the above-identified problems. However, because the primary function of the conventional dry corn mill process (13) is to facilitate the production of a lowered-fat grit or meal for the production of food products such as cereal, table grits or the like, the conventional dry corn mill process (13) including hardware and methods of utilizing the hardware have not been optimized to provide a corn endosperm fraction (14) for introduction into an ethanol production process (4). As such, overall process yield of the corn endosperm fraction (14) useful in the ethanol production process (4) has never been the primary goal of the dry corn mill process (13) and as such corn endosperm recovery is typical sacrificed to increase corn endosperm purity. However, loss of corn endosperm in the context of an ethanol production process (4) solely to increase corn endosperm purity can result in significant economic losses.

Understandably, recovery of corn endosperm in the corn endosperm fraction (14) increases in the context of conventional dry corn mill processes (13) and other corn mill processes which generate a corn bran fraction (15), corn germ fraction (16), and corn endosperm fractions, the amount of corn germ along with the corresponding amount of corn germ oil in the endosperm fraction (14) may also increase and enter the ethanol production process (4). The increased amount of corn germ and corn oil introduced into the ethanol production process (4) may proportionately decrease the amount of corn endosperm (14) processed per unit volume capacity of the ethanol production process (4), increases the amount of DDG produced but correspondingly decreases the percent protein by weight of the DDG (7). Accordingly, the DDG (7) or DDGS (8) having increased fat content may have a decreased value as an animal feed. Additionally, an increase in fat content of the DDG (7) can make the DDG (7) unacceptable as a feed for poultry and fish, as above described.

To address the unresolved problems of conventional corn mill processes and conventional dry corn milling above-described the instant inventive dry corn fractionation system generates isolated corn fractions including a bran fraction, a germ fraction, and an endosperm fraction with high purity and at high yield which can be utilized independent of the other in proportioned recombination in the ethanol production process.

II. SUMMARY OF THE INVENTION

Accordingly, a broad object of the invention can be to provide a dry corn fractionation system which operates to isolate a corn bran fraction, a corn germ fraction, and a corn endosperm fraction which have a greater purity coupled with a greater yield than conventional dry corn milling.

Another broad object of the invention can be to provide a corn endosperm fraction of not less than about seventy percent purity by weight coupled with an overall corn endosperm loss of not greater than about six percent by weight or even not greater than four percent by weight.

Another broad object of the invention can be to provide a dry corn fractionation system which includes as an initial step kernel breakage which generates a population of corn particles which have a greater size whether individually or as a population than compared to the first kernel breakage step of a conventional corn mill process.

Another broad object of the invention can be to provide a kernel breaker which operates to provide the kernel breakage which generates the population of corn particles which have a greater size whether individually or as a population than compared to the first kernel breakage step of a conventional corn mill process.

Another broad object of the invention can be to provide a first aspiration step and a second aspiration step coupled directly after the kernel breakage step and directly before a sifting step to remove bran and fines containing moisture to increase the efficiency of the sifting step.

Another broad object of the invention can be to provide a bran finishing step coupled directly after the second the second aspiration step which operates to remove corn endosperm associated with the bran fraction aspirated from second aspirator and return the removed corn endosperm to the sifting step.

Another broad object of the invention can be to provide a first density separation and a second density separation coupled directly after the sifting step the second density separation being the final step in the dry corn mill system which yields a corn endosperm fraction of greater than seventy percent purity by weight with a overall loss of corn endosperm fraction of not greater than about four percent by weight.

Another broad object of the invention can be to couple the corn fractionation system to an ethanol production process to decrease thermal energy consumption, increase ethanol production capacity, and produce a high protein dried fractionated corn gluten meal whether independently or in various combinations and permutations.

Naturally, further objects of the invention are disclosed throughout other areas of the specification, drawings, and claims.

IV. DETAILED DESCRIPTION OF THE PREFERRED EMBODIMENTS

A dry corn fractionation system which operates to produce an endosperm fraction which can be concurrently of greater purity at greater yield than the corn milling or dry corn milling processes.

Figure 3:
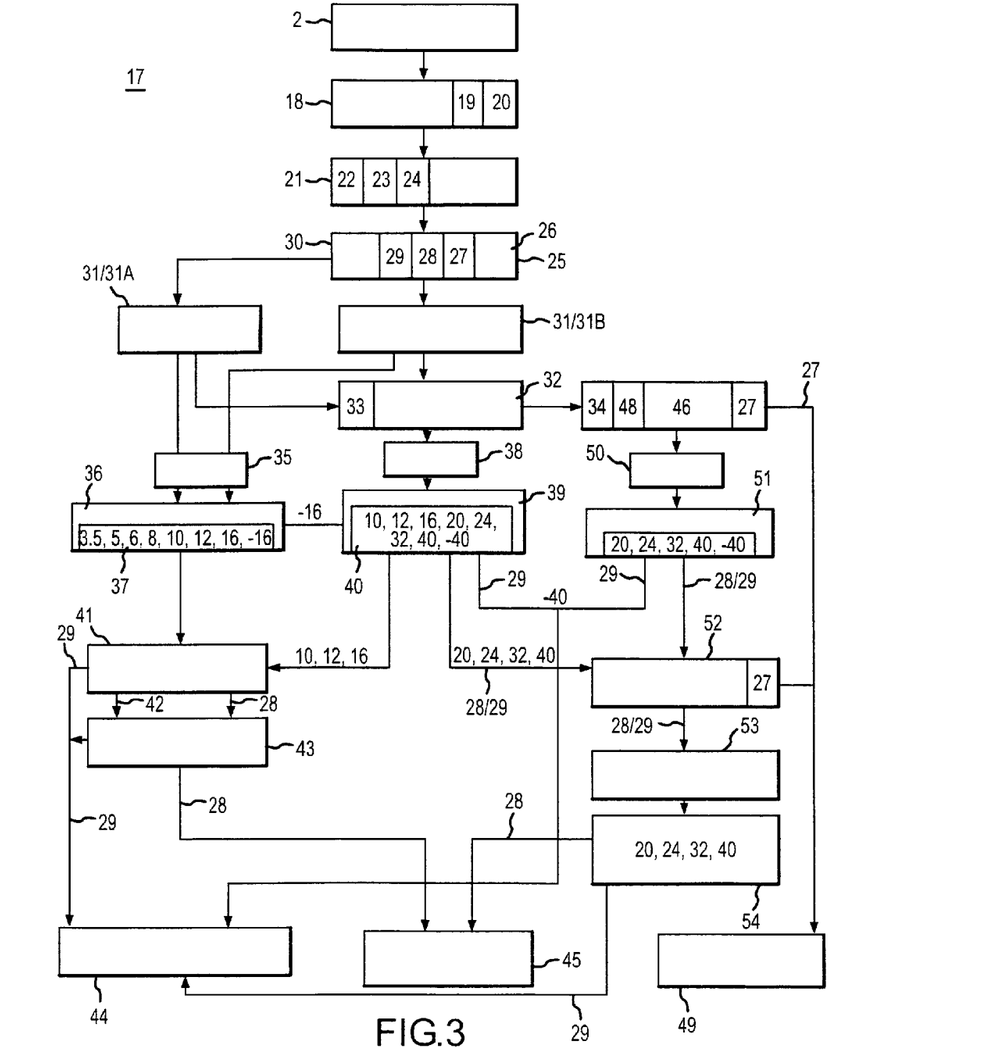
FIG. 3 is a block flow diagram of the inventive corn fractionation system which generates corn fractions coupled to a ethanol production process.

First referring primarily to FIG. 3, the dry corn fractionation system (17) whole corn (2) can be received and accepted by a corn cleaner (18). Whole corn (2) can move along a first sloping deck of the corn cleaner (18) having a plurality of holes. Whole corn (2) can pass through the holes onto an second sloping deck thereby removing material larger than a kernel of whole corn (2). The whole corn (2) then moves along the second sloping deck having holes of lesser size then a kernel of whole corn (2) thereby removing material smaller than a kernel of whole corn (2). The corn cleaner (18) can further include a cleaner aspirator (19). Whole corn (2) then passes through the cleaner aspirator (19) (as a non-limiting example a Series E six path unit available from Kice Industries, Inc., 5500 North Mill Heights Drive, Wichita, Kans.) to remove material having lesser density than a kernel of whole corn (2). The corn cleaner (18) can further include a de-stoner (20) which removes materials of greater density than a kernel of whole corn (2). The term "whole corn" as used herein broadly encompasses kernels of corn removed from the cob regardless of the variety or grade. Additionally, it is not intended that the example of a corn cleaner (18) be limited to above-described configuration and any manner of corn cleaning which results in whole corn (2) which is substantially free of materials that are not whole corn (2) can be utilized with the various embodiments of the dry corn fractionation system (17).

The whole corn (2) substantially free of other materials can be accepted by a corn temper process (21). The whole corn (2) cleaned of other materials can be transferred by a conveyor (22) (as a non-limiting example a Bi-Mix 30-55/180-22 available from GBS Group S.p.a, Corso Uniti, 7, Padova, Italy). As the whole corn (2) moves up the inclined conveyor (22), water and steam can be introduced to the whole corn (2) and mixed by the conveyor (22) (by paddles, screws, or the like). The whole corn (2) leaves the conveyor and drops into a temper tank (23). The whole corn (2) resides in the temper tank (23) for a duration of time of between about five minutes and fifteen minutes to allow the water to be distributed over the entire kernel of whole corn (2) and absorbed by the bran coat until the bran coat reaches a pre-selected target moisture.

Figure 4:
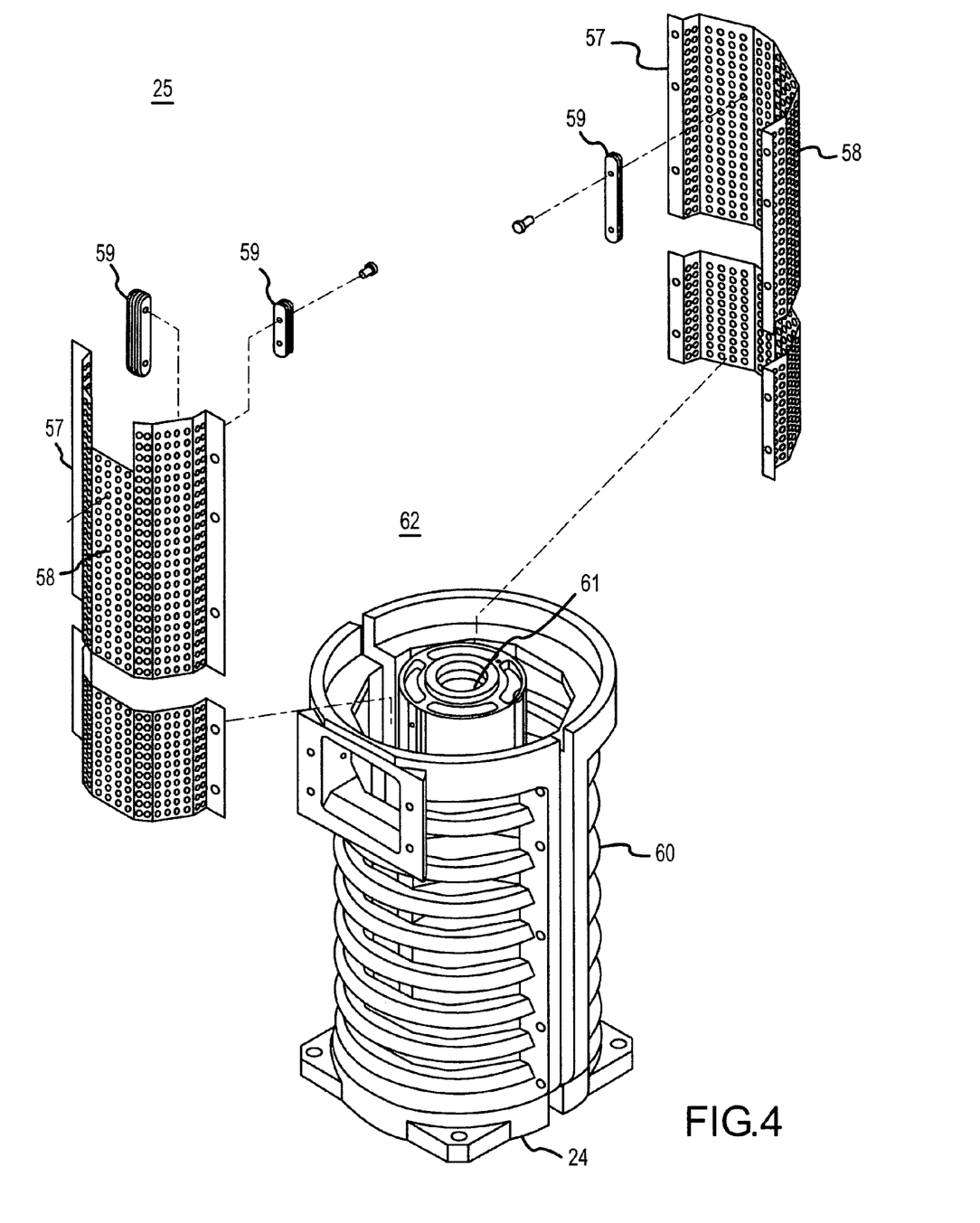
FIG. 4 is an exploded view of a part of a Satake Maize Degermer modified to produce an embodiment of the dry corn mill granulation.

Again referring primarily to FIGS. 3 and 4, after tempering a plurality of kernels of whole corn (24) can be accepted by a kernel fracture assembly (25) which breaks the whole corn (2) into a plurality of corn particles (26). The initial breakage of the plurality of kernels of whole corn (24) which generates a mixture of a plurality of corn bran particles (27), a plurality of corn germ particles (28) and a plurality of corn endosperm particles (29) affects the success of all subsequent fractionation steps in the inventive dry corn fractionation system (17). Numerous and varied kernel fracture assemblies (25) can be utilized to generate the plurality of corn particles (26) having a size or a range of sizes suitable for use in the dry corn fractionation system (17). One non-limiting kernel fracture assembly (25) suitable for use in the inventive dry corn fractionation system (17) can be a modified Satake Maize Degermer, model VBF 10AM-L available from Satake Corporation, 2-30, Saijo, Nishiho-machi, Higashihiroshia-shi, Hiroshima, Japan.

Now referring primarily to FIG. 4, the Satake Maize Degermer (shown in part) can be altered or modified to produce the plurality of particles (26) suitable for use with the inventive dry corn fractionation system (17) by replacing the conventional slotted screens having a plurality of 0.8 mm slots with perforated screens (57) each having a plurality of perforations (58) of about the same number as the conventional slots and each being substantially circular having diameter in the range of between about 5 millimeters ("mm") to about 10 mm with certain embodiments having diameter of between about 6 mm to about 9 mm and with certain embodiments having a diameter of between about 6 mm to about 8 mm. The non-limiting embodiment of the perforated screens as shown in the figure can have a plurality of perforations (58) of be about 7 mm. However, the desired size distribution of the plurality of corn particles (26) may be obtained utilizing other perforation configurations and the invention is not limited solely to substantially circular perforations but to any configuration of perforation which can yield the inventive particle size distribution described herein. The plurality of perforations (58) can have be located at the same or similar locations of the prior conventional slots, however, the invention is not so limited and the location or placement pattern of the plurality of perforations (58) can be any location or placement which yields the inventive particle size distribution described herein.

Additionally, the conventional 4 mm breaker bars (often referred to as "clickers") can be replaced with modified breaker bars (59) of between about 6 mm to about 10 mm at substantially the same locations as the conventional clickers, or replacing both (see FIG. 4 which shows the modified screens (58) with modified breaker bars (59) which can be fit to a conventional Satake Maize Degermer). Again, based on the configuration and placement of the plurality of perforations (58), embodiments of the invention can utilize unmodified clickers, or modified breaker bars (59) which generate the particle size distribution of the plurality of particles (26) described herein. Alternately, as to certain embodiments the clickers can be modified and the plurality of perforations configured to the extent necessary to generate the particle size distribution described herein. As a particular embodiment of the invention as shown in the figures, both the plurality of perforations (58) and the modified breaker bars (59) can be utilized to produce the particle size distribution described herein.

With respect to the operation of the modified Satake Maize Degermer, the plurality of kernels of whole corn (24) enter the bottom of a substantially vertical cylinder (60) and become located between the surface of a rotating drum (61) and the inside walls (62) of the steel cylinder (60) to become fractured by kernel on steel impact and by kernel on kernel impact into the plurality of corn particles (26). A part of the plurality of corn particles (26) pass through the perforations in the walls of the steel cylinder (referred to as the "throughs"). The remaining plurality of corn particles (26) pass over the top of the steel cylinder (referred to as the "tails"). FIG. 4 does not show the additional parts of the Satake Maize Degermer which can be utilized without modification as shown in the company catalog.

By modifying the Satake VBF Maize Degermer as above-described, the size distribution of the plurality of corn particles (26) generated substantially changes with respect to the "tailstock" and the "through stock". Referring first to Table 1 below fracturing of a plurality of whole corn kernels (24) with a conventional Satake VBF can result in amount of "tailstock" of about 73 percent by weight of the plurality of corn kernels (25) introduced into the Satake VBF Degermer. The size distribution of the "tailstock" held by a 3.5 wire, a 4 wire, a 5 wire, a 6 wire, an 8 wire, or a 10 wire sifter and the amount passing through the 10 wire sifter to the pan are shown as percents by weight of the total weight of the plurality of whole corn kernels (24) introduced into the Satake VBF Maize Degermer and as a percent of the total weight of the tailstock generated. Similarly, as shown by Table 2 fracturing of a plurality of whole corn kernels (24) results in a conventional amount of "throughstock" of about 22 percent by weight of the plurality of corn kernels (24) introduced into the Satake VBF Degermer. The size distribution of the "throughstock" held by a 6 wire, a 4 wire, a 10 wire, a 14 wire, an 18 wire, a 24 wire, and a 40 wire sifter, and passing through the 40 wire sifter to the pan are shown respectively as a percent by weight of the total weight of the plurality of whole corn kernels (24) introduced into the Satake Degermer and as a percent total weight of the throughstock generated.

Now comparing the size distribution of the plurality of particles (26) conventionally generated to the size distribution of the plurality of particles (26) generated by the non-limiting example of the modified Satake VBF Maize Degermer as above described and utilized in the inventive dry corn fractionation system (17), it can be understood that the size distribution for the "tailstock" and the "throughstock" generated by the modified Satake VBF Maize Degermer falls in a narrower range of particle size with lesser of the plurality of corn particles (26) held by the 3.5 wire screen (typically re-fractured) and with a reduction in the plurality of particles (26) having a size lesser than can be held by a 10 wire screen. As such, the vast majority of the plurality of particles (26) produced by the inventive corn fracture assembly (25) fall in the range of −3.5 wire (falling through a 3.5 wire screen) and +10 wire (retained by a 10 wire screen). As compared to the conventional range of −3.5 wire and +40. Note, that the amount of −10 particles (falling through a 10 wire screen) for the tailstock and the through stock combined is reduced by about 15 percent to about 25 percent over the conventional corn fracture process. Also the amount of fines −40 wire (falling through a 40 wire screen) produced by the inventive corn fracture assembly is substantially reduced. Reduction in the amount fines significantly lower water content of the plurality of particles and allows subsequent steps in the inventive dry corn fractionation system (17) to operate without or a reduced aggregation of particles.

TABLE 1

Conventional Corn Particle Size Distribution Of Tailstock Generated By A Conventional Satake Maize Degermer.

| Wires/In. | % Retained Of Total Whole Corn | % Total Retained Of Tailstock |
|---|---|---|
| Sifted Tails | | 72.98% |
| 3.5 | 31.77% | 23.19% |
| 4 | 7.75% | 5.66% |
| 5 | 22.38% | 16.33% |
| 6 | 15.28% | 11.15% |
| 8 | 10.92% | 7.97% |
| 10 | 5.35% | 3.90% |
| pan (−10) | 6.55% | 4.78% |
| Total | 100.00% | 72.98% |

TABLE 2

Conventional Corn Particle Size Distribution Of Throughstock Generated By A Conventional Satake Maize Degermer.

| Wires/In. | % Retained Of Total Whole Corn | % Total Retained Of Tailstock |
|---|---|---|
| Sifted Throughs | | 21.51% |
| 6 | 0.00% | 0.00% |
| 10 | 0.57% | 0.12% |
| 14 | 1.00% | 0.22% |
| 18 | 8.14% | 1.75% |
| 24 | 15.14% | 3.26% |
| 40 | 28.43% | 6.11% |
| pan (−40) | 46.71% | 10.05% |
| Total | 100.00% | 21.51% |

TABLE 3

Corn Particle Size Distribution Of Tailstock Generated By A Modified Satake Maize Degermer.

| Wires/In. | % Retained Of Total Whole Corn | % Total Retained Of Tailstock |
|---|---|---|
| Sifted Tails | % | 24.87% |
| 3.5 | 28.80% | 7.16% |
| 4 | 15.72% | 3.91% |
| 5 | 38.54% | 9.58% |
| 6 | 12.17% | 3.03% |
| 8 | 3.04% | 0.76% |
| 10 | 1.01% | 0.25% |
| pan (−10) | 0.71% | 0.18% |
| Total | 100.00% | 24.87% |

TABLE 4

Corn Particle Size Distribution Of Throughstock Generated By Modified Satake Maize Degermer.

| Wires/In. | % Retained Of Total Whole Corn | % Total Retained Of Tailstock |
|---|---|---|
| Sifted Throughs | % | 53.90% |
| 3.5 | 1.28% | 0.69% |
| 4 | 4.84% | 2.61% |
| 5 | 28.31% | 15.26% |
| 6 | 29.02% | 15.64% |
| 8 | 17.78% | 9.58% |

TABLE 4-continued

Corn Particle Size Distribution Of Throughstock Generated By Modified Satake Maize Degermer.

| Wires/In. | % Retained Of Total Whole Corn | % Total Retained Of Tailstock |
|---|---|---|
| 10 | 9.25% | 4.98% |
| pan (−10) | 9.53% | 5.14% |
| Total | 100.00% | 53.90% |

Understandably, numerous and wide variety of kernel fracture assemblies (25) can be adjusted or modified to generate the in the dry corn mill fractionation system (17) to generate a plurality of corn particles (26) having a comparable particle size distribution to Tables 3 and 4 (the term "comparable" meaning the combined weight percent of the corn particles retained by screens between about 4 wire screen and about a ten wire screen to the total weight of the unfractured whole corn (2) is not reduced by an amount greater than about 10 percent) whether in a plurality of particle streams, two streams such as "tailstock" and "throughstock", or as a single stream so long as the particle size distribution over the streams generated by kernel fracture assembly remains comparable or yields an even greater weight percent of the plurality of particles (26) of +4 to about +10 than described herein. Understandably the goal is to generate a plurality of particles (26) which are the fewest in number and greatest in size which can still be utilized to separate the plurality of kernels of whole corn (24) into the constituent parts including corn bran, corn germ and corn endosperm. (the inventive "dry corn mill granulation") (30). Production of the dry corn mill granulation (30) is considered to be encompassed by or a part of the inventive dry corn fractionation system (17), or as an isolated step an invention in itself without more. The dry corn mill granulation having not been described before the instant patent application and providing a solution to a substantial problem in corn fractionation and the problem of developing a corn fractionation system compatible with ethanol production.

Again referring primarily to FIG. 3, the plurality of particles (26) generated by the corn fracture assembly (25) (which as to certain embodiments of the invention can have the size distribution of the dry mill granulation (30) above-described) can be passed through a first aspirator (31) (or a plurality of first aspirators in parallel) and a second aspirator (32) (or a plurality of second aspirators in parallel) to separate an aspirated stream of the plurality of corn bran particles (27) from a non-aspirated stream comprising a mixture of the plurality of corn endosperm particles (29) and the plurality of corn germ particles (28). The aspirated stream of the plurality of corn bran particles (27) can contain certain particles of corn endosperm attached to a part of the plurality bran particles (27) and certain particles of corn endosperm and certain particles of corn germ of sufficiently low mass to be aspirated by the first aspirator (31). As such, the non-limiting embodiment of the aspiration step shown in FIG. 3, the "tails" and the "throughs" from kernel fracture assembly (25) of the modified Satake Degermer each separately pass separately through a first aspirator (31A)(31B) to generate a mixture of the plurality of corn endosperm particles (29) and the plurality of corn germ particles (28) and a first aspirated plurality of corn particles (33). The first aspirated plurality of corn particles (33) passes through the second aspirator (32) to generate a mixture of the plurality of corn endosperm particles (29) and the plurality of corn germ particles (28) and a second aspirated plurality of corn particles (34) which largely contains the plurality of corn bran particles (27) but also contains some amount of the plurality of corn germ particles (28) and some amount of the plurality of corn endosperm particles (29). A non-limiting example of the first aspirator(s) (31) and the second aspirator(s) (32) can be a Kice, Series E six path unit available from Kice Industries, Inc., 5500 North Mill Heights Drive, Wichita, Kans. The determination of the correct air setting for the first aspirator (31A) through which the "tails" pass and the first aspirator (31B) through which the "throughs" pass can be made by achieving a particle profile which includes mixture of the plurality of corn endosperm particles (29) and plurality of corn germ particles (28) comprising about 95% of the non-aspirated stream by weight of each of the first aspirators (31). An advantage of utilizing a first aspiration step and a second aspiration step over conventional process methods can be removal of the plurality of corn bran particles (27) and part of the plurality of corn endosperm particles (29) and part of the plurality of corn germ particles (27) of sufficiently low mass to be aspirated in the first and second aspirated plurality of corn particles (33)(34) which contain the vast majority of the water content in the plurality of particles (26) delivered from the corn fracture assembly (25) which allows for more ready sifting of the non-aspirated mixture (35) of the plurality of corn endosperm particles (29) and the plurality of corn germ particles (28).

Again referring primarily to FIG. 3, the non-aspirated mixture (35) of the plurality of corn endosperm particles (29) and the plurality of corn germ particles (28) from the first aspirator(s) (31)(31A)(31B) can be accepted by a first sifter (36) which generates a plurality of streams of sifted particles (37) by retaining a part of the plurality of corn endosperm particles (29) and a part of the plurality of corn germ particles (28) on a plurality of screens between the range of about 3.5 wires per inch to about 16 wires per inch. A certain non-limiting embodiment of the first sifter (36) can have a 3.5 wire screen, a 5 wire screen, a 6 wire screen, a 10 wire screen, a 12 wire screen, and a 16 wire screen although other combinations of screens in the range could also be utilized. Similarly, the non-aspirated mixture (38) of the plurality of corn endosperm particles (29) and corn germ particles (28) from the second aspirator (32) can be accepted by a second sifter (39) to generate a plurality of streams (40) of endosperm particles (29) and corn germ particles (28) by retaining a part of the plurality of corn endosperm particles (29) and a part of the plurality of corn germ particles (28) on a plurality of screens between the range of about 10 wires per inch to about 40 wires per inch. A certain non-limiting embodiment of the second sifter (39) can have a 10 wire screen, a 12 wire screen, a 16 wire screen, a 20 wire screen, a 24 wire screen, a 32 wire, and a 40 wire screen although other combinations of screens in the range can be utilized. The second sifter (39) in the embodiment shown can also accepts the −16 particles (particles falling through a 16 wire screen) from the first sifter (36) (although these corn particles not retained by the first sifter (36) will be the pass through of the smallest selected screen). As a non-limiting example, a Great Western "HS" Sifter available from Great Western Manufacturing, 2017 South 4$^{th}$ Street, Leavenworth, Kans. 66048-0149 can be suitable for use as above-described.

Of the plurality of streams of sifted particles (37)(40) generated by the first sifter (36) and the second sifter (39) of greater than about 16 wire can be accepted by a corresponding plurality of first gravity separators (41). In the non-limiting example provided above each of the plurality of streams of sifted particles (37)(40) retained by the 5 wire screen, the 6 wire screen, the 8 wire screen, the 10 wire screen and the 16 wire screen can be accepted by a corresponding one of the plurality of first gravity separators (41). Each of the plurality of first gravity separators (41) can generate three separator streams including a plurality of corn endosperm particles (29); a mixture of corn endosperm particles and corn germ particles (42), and a plurality of corn germ particles (28). The separator streams which include the plurality of corn endosperm particles (29) from each first separator (41) can be accepted in a corn endosperm fraction storage unit (44). The separator streams including the mixture of corn endosperm particles and the plurality of corn germ particles (42), and the plurality of corn germ particles (28) can each be accepted by a corresponding one of a plurality of second gravity separators (43) each of which generates two second separator streams including the plurality of corn endosperm particles (29) and the plurality of corn germ particles (28). The plurality of corn endosperm particles (29) can be accepted by the corn endosperm fraction storage unit (44) and the plurality of corn germ particles (28) accepted by a corn germ fraction storage unit (45). A non-limiting example of a gravity separator can be a Forsberg Vacuum Gravity Separator, Model 50-VMS available from Forsberg, Inc., P.O. Box 510, 1210 Pennington Avenue, Thief Rivers Falls, Minn. 56701. A plurality of corn germ particles (28) can be retained by the second sifter on screens in between the range of about 20 wire to about 40 wire which can be accepted by third aspirator (46).

The second aspirated plurality of corn particles (34) from the second aspirator (32) can be accepted by a corn bran finisher (46). The corn bran finisher (46) operates to remove an amount of bound corn endosperm (48) from the plurality of corn bran particles (27) to generate an unbound mixture of the plurality of corn endosperm particles and the plurality of corn germ particles (50) and a stream of corn bran particles (27). As a non-limiting example, a Kice Bran Finisher, Model BF42 can be utilized to accept the second aspirated plurality of corn particles (34).

The stream of the plurality of corn bran particles (27) can be accepted by a corn bran fraction storage unit (49). The unbound mixture of the plurality of corn endosperm particles and the plurality of corn germ particles (50) can be accepted by a third sifter (51) having a range of screens between about 20 wires per inch and 40 wires per inch. A non-limiting example of a third sifter (51) can provide a 20 wire screen, a 24 wire screen, a 32, wire screen, and a 40 wire screen. A suitable third sifter (51) can be a Great Western "HS" Sifter. The plurality of corn germ particles (28) retained by the third sifter (51) in the range of between about the 20 wire screen and the 40 wire screen can be accepted by a third aspirator (52) along with the plurality of corn germ particles (28) retained by the second sifter (39) in the range of between about the 20 wire screen and the 40 wire screen. The plurality of corn endosperm particles (29) passing through the 40 wire screen of the second sifter (39) and the third sifter (51) can be accepted by the corn endosperm fraction storage unit (44).

The non-aspirated stream from the third aspirator (52) comprised largely of a plurality of corn germ particles (28) can be accepted by a plurality of roller mills (53) which operate to increase the size of the plurality of corn germ particles (28) and reduce the size of the plurality of corn endosperm particles (29). A suitable non-limiting example of a roller mill can be a Model 100/30-4A Pick-Up available from GBS Group S.p.a, Corso Stati, 7-Padova-Italy. The plurality of corn germ particles (28) and the plurality of corn endosperm particles (29) from each roller mill (53) can be accepted by a fourth sifter (54) having a plurality of screens in the range of between about 20 wires per inch and about 40 wires per inch. The plurality of corn germ particles (28) retained by the plurality of screens between about 20 wires per inch and about 40 wires per inch can be accepted by the corn germ fraction storage unit (45). The plurality of corn endosperm particles (29) which pass through the screen having about 40 wires per inch can be accepted by the corn endosperm storage unit (44).

The inventive dry corn fractionation system (17) can produce end material balances by weight percent for each corn fraction (44)(45)(49), as follows:

Germ %: about 8.0 to about 9.0
Bran %: about 6.0 to about 6.4
Endosperm %: about 85.0 to about 86.0

In addition to the end material balances by weight percent for each fraction (44)(45)(49), the inventive dry corn fractionation system (17), can as to certain embodiments produce each corn fraction with advantageous ratios of fat, fiber, and starch by weight percent, as follow:

|  | Fat % | Fiber % | Starch % |
|---|---|---|---|
| Germ Fraction (45) | 18% min. | 25% max. | 30.0% max. |
| Bran Fraction (49) | 6% max. | 75% min. | 25.0% max. |
| Endosperm Fraction (44) | 2.5% max. | 2.0% max. | 82.5% min. |

Additionally, certain embodiments of the inventive dry corn fractionation system (17) can achieve these advantageous ratios and material balances concurrently which allows a high purity endosperm fraction (44) of at least about 82% with starch loss (compared to clean whole corn (2)) of not greater than about 4%.

Figure 5:
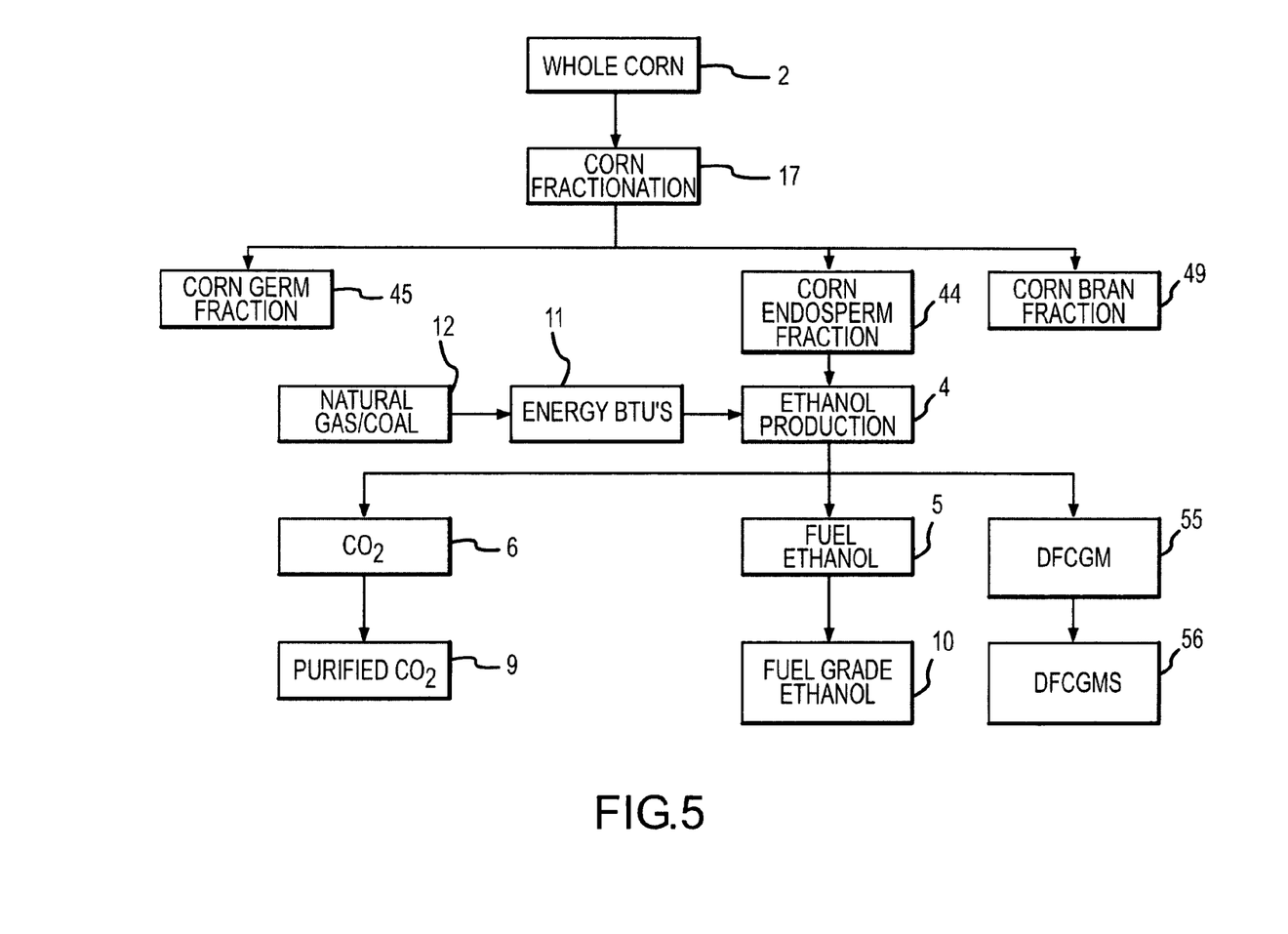
FIG. 5 is a block flow diagram of an embodiment of the inventive dry corn mill fractionation system.

Now referring primarily to FIG. 5, the corn endosperm fraction (44) generated by the inventive dry corn fractionation system (17) can be coupled to a various configurations of an ethanol production process (4) to increase the amount of ethanol (5) produced, reduce the amount of thermal energy used per unit of ethanol (5) produced, reduce the cost per unit of ethanol (5) produced, and to produce in substitution of the DDG an amount of a high protein dried fractionated corn gluten meal (55) ("DFCGM") which can be mixed with solubles to produce a high protein high protein dried fractionated corn gluten meal with solubles (56) ("DFCGMS"). Embodiments of suitable configurations of the ethanol production process (4) which can be coupled to the endosperm fraction (44) generated by the inventive corn fractionation system (17) are described for example by Patent Cooperation Treaty Application No. PCT/US2006/045193, hereby incorporated by reference.

Figure 6:
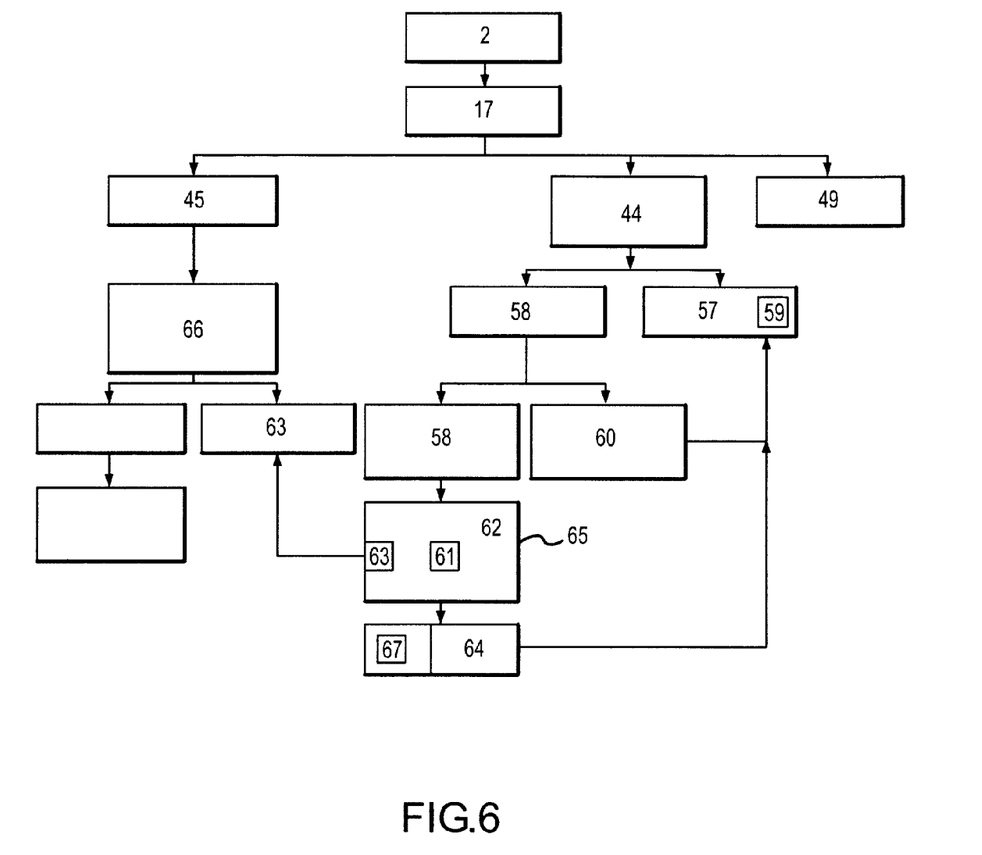
FIG. 6 is a block flow diagram of an generic embodiment of a corn fractionation process which further includes a corn endosperm fraction split into a non-extracted endosperm stream and an extracted endosperm stream.

Now referring primarily to FIG. 6, the corn endosperm fraction (44) generated by the inventive dry corn fractionation system (17) (or generated by conventional dry corn mill processes (13) (see for example FIG. 2), or generated by other corn mill processes which process whole corn (2) to separate at least a part of the corn bran (49) and at least a part of the corn germ (45) to provide an endosperm fraction (44) of greater purity) can be further separated to provide at least one non-extracted endosperm stream (57) (also referred to as "a first endosperm stream") and at least one extracted endosperm stream (58) (also referred to as "a second endosperm stream"). Separation of the corn endosperm fraction (44) into at least one non-extracted endosperm stream (57) and at least one extracted endosperm stream (58) can provide the at least one non-extracted endosperm with a substantially lesser fat content the at least one extracted endosperm stream (58). Understandably, the at least one non-extracted stream (57) and the at least one extracted stream (58) can be generated by combining a plurality of subfractions from sifting and density separation processes above-described (or other method of separating the corn endosperm fraction) to establish in each of the at least one non-extracted endosperm stream (58) and the at least one extracted endosperm stream a predetermined fat content.

Again referring primarily to FIG. 6, as but one non-limiting example, the non-extracted endosperm stream (57) can provide a purity of not less than about 85 percent by weight starch and including less than about 1.5 percent by weight fat which results primarily from an amount of comixed corn germ (59). Correspondingly, the extracted endosperm stream (58) can provide a purity of less than about 85 percent by weight starch and including more than about 1.5 percent by weight fat primarily as a result of an amount of comixed corn germ (59). Understandably, the non-extracted endosperm stream (57) can provide a greater or lesser purity and a corresponding greater or lesser amount of fat depending upon the end result desired and the method utilized to separate the corn germ (45) from the corn endosperm (44). Additionally, the extracted endosperm stream (57) can have a correspondingly greater or lesser purity and a corresponding greater or lesser amount of fat depending upon the end material balance of the non-extracted endosperm stream (58).

Again referring to FIG. 6, as to certain embodiments of the inventive dry corn fractionation system (17), the extracted endosperm stream (58) can be further separated based on particle size to remove an amount of non-extractable endosperm particles (60). Non-extractable endosperm particles (60) are typically those endosperm particles which are incompatible with a particular subsequent extraction process or step in the operation of an endosperm corn oil extraction system (65). As but one non-limiting example, the non-extractable endosperm particles (60) can be incompatible due to a lesser size of such non-extractable endosperm particles (60) restricting flow of an extractant within an extraction vessel of the endosperm extraction system (65). As to the non-limiting embodiments of the invention shown in FIG. 6, the non-extractable endosperm particles (60) can be removed by sifting and encompass those particles which fall through a 40 wire screen (−40). The non-extractable particles (60) can be combined with non-extracted endosperm stream (57).

An amount of the extracted endosperm stream (61) can be fluidicly coupled to an amount of extractant (62) (such as supercritical carbon dioxide) which can transfer an amount of the corn oil (63) from the amount of the extracted endosperm stream (61) to the amount of extractant (62). Transfer of the amount of corn oil (63) from the extracted endosperm stream (58) to the amount of extractant (62) results in an amount of endosperm-germ cake (64). The endosperm-germ cake (64) which contains a reduced amount of corn oil (63) (or contains the remaining amount of corn oil (63)) can be combined with the non-extracted endosperm stream (57).

Again referring primarily to FIG. 6, extraction of the extracted endosperm stream (58) with an amount of extractant (62) to produce an amount of corn oil (63) can be achieved in the endosperm oil extraction system (65) separate from and without dependence upon the extraction of an amount of the corn germ fraction (45) in a corn germ oil extraction system (66) to produce an amount of corn oil (63). In those embodiments of the invention which further include extraction of corn oil (63) from the corn germ fraction (45), the corn germ oil extraction system (66) can involve conventional apparatus and methods of extracting the amount of corn oil (63) from an amount of the corn germ fraction (45) or can involve inventive apparatus and methods described for example in U.S. patent application Ser. No. 11/716,838, hereby incorporated by reference herein. The amount of corn oil (63) generated by extraction of an amount of the extracted endosperm stream (61) and the amount of corn oil (63) generated by extraction of an amount of the corn germ fraction (45) can be combined for refining. The endosperm-germ cake (64) resulting from extraction of the amount of the extracted endosperm fraction (62) can contain a reduced amount of corn oil (67) (or contains the remaining amount of corn oil after extraction).

The term "corn oil" as used herein includes a wide range of compositions as mixtures of neutral oils, fatty acids, and a greater or lesser amounts of undesired impurities. The undesired impurities can include one or more of: free fatty acids (FFA) from the degradation of the neutral oils by hydrolysis; phosphatids (hydratable and non-hydrateable); organic compounds which can have certain colors, flavors or odors; particulates, or an amount of unremoved extractant entrained in the extraction materials obtained by extraction of the corn germ fraction (45), the extracted endosperm stream (58), or an amount of the extracted endosperm stream (61), or the like.

Figure 7:
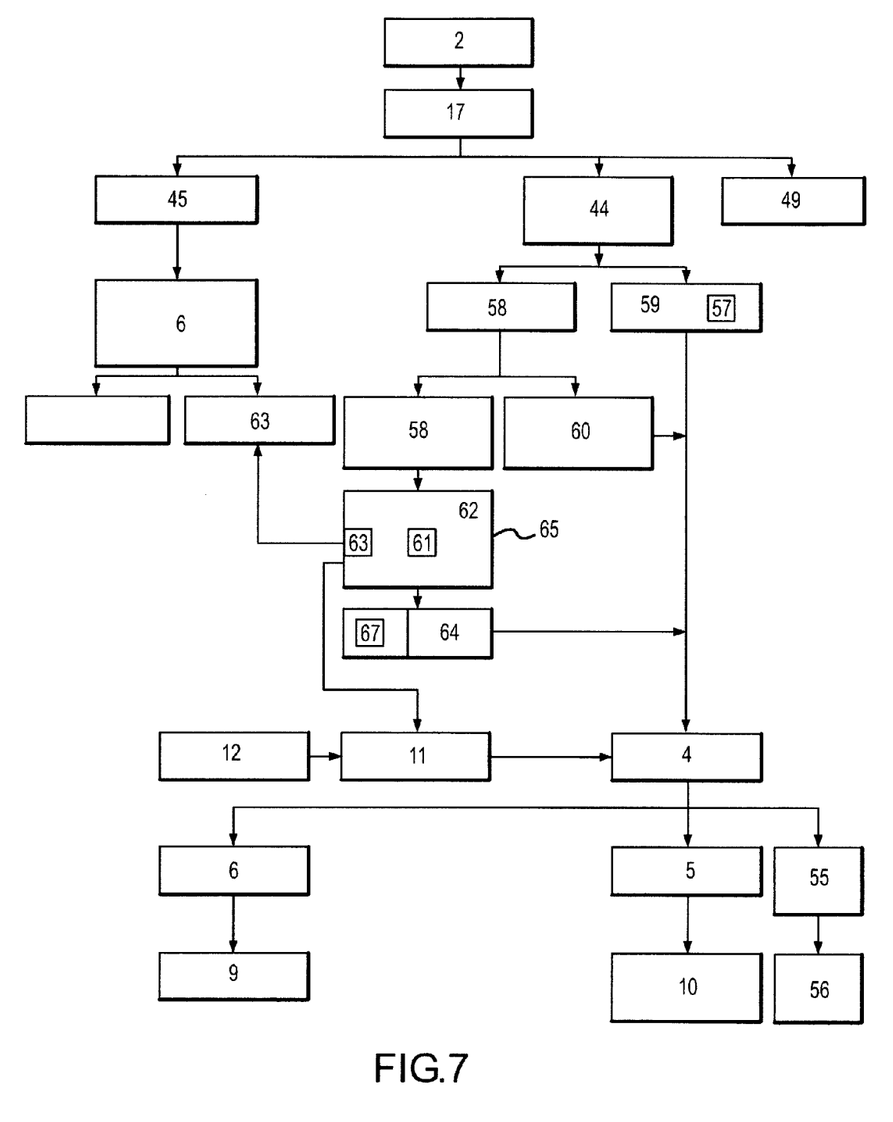
FIG. 7 is a block flow diagram of a specific embodiment of the inventive corn fractionation system shown in FIG. 3 which further includes the corn endosperm fraction split into a non-extracted endosperm stream and an extracted endosperm stream both coupled to a ethanol production process.

Now referring primarily to FIG. 7, as to certain embodiments of the invention the amount of endosperm-germ cake (64) can be combined with the at least one non-extracted endosperm stream (57) which can also include the amount of non-extractable endosperm particles (60). The combined endosperm streams can be further introduced into the ethanol production system (4).

EXAMPLE 1

As a first non-limiting example of the endosperm corn oil extraction system (65), 22.52 grams of an amount of the extracted endosperm stream (61) (also referred to as the feedstock) providing a −24 wire+40 wire particle size (particles fell through a 24 wire screen but were retained by a 40 wire screen) was introduced into an extraction vessel and extracted with an amount of carbon dioxide for 40 minutes at a pressure of about 9000 pounds per square inch at a temperature of 110° C. at a flow rate of 6 liters per minute (the "extraction event").

Figure 8:
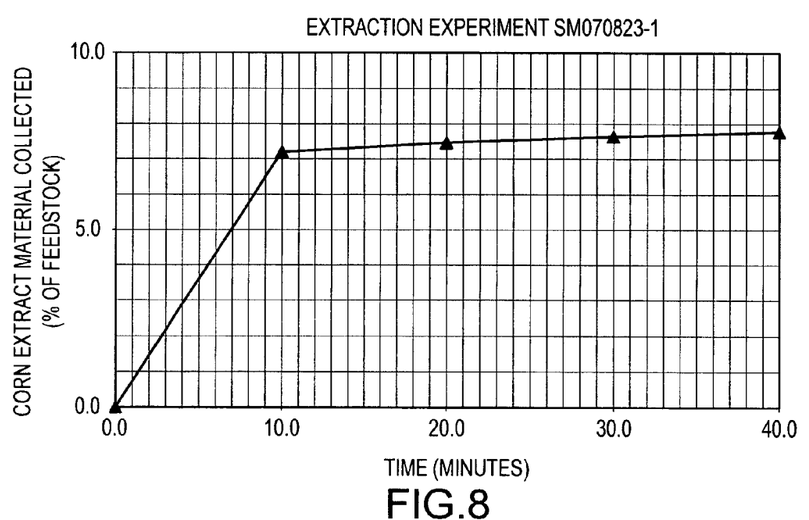
FIG. 8 provides a graph which plots the amount of corn oil extracted as a weight percent of the amount of an extracted corn endosperm stream against the duration of time.

Now referring to FIG. 8, which shows a graph of the results of the extraction event as the amount of corn oil (63) (or corn endosperm extraction material collected reported as a percent weight of the feedstock) over the 40 minute duration of the extraction event. A total amount of 1.8 grams of corn oil (63) was extracted (about 7.8% of feedstock by weight of feedstock). As can be understood from the graph shown in FIG. 8, substantially all the corn oil (63) extractable from the amount of the extracted endosperm stream (61) (feedstock) can be obtained with the first ten minute interval of the extraction event.

Figure 9:
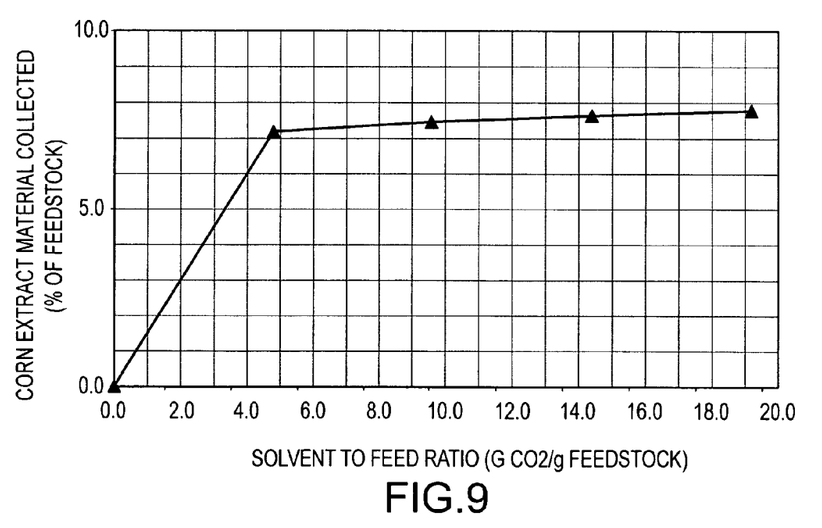
FIG. 9 provides a graph which plots the amount of corn oil extracted as a weight percent of the amount of an extracted corn endosperm stream against the extractant to feedstock ratio.

Now referring to FIG. 9 which shows a graph of the results of the amount of corn oil (63) (or corn endosperm extraction material collected reported as a percent weight of the feedstock) over the amount of carbon dioxide utilized per gram of the feedstock, it can be understood that lesser and greater extraction efficiencies can be determined for a particular set of extraction conditions and reported as an extractant to feedstock ratio. For example, for extraction conditions utilizing and amount of carbon dioxide at 9000 psi at about 110° C. a comparably greater efficiency extraction can be achieved at about 4.5:1 to about 5.5:1 extractant to feedstock ratio to produce about 7% of feedstock by weight of extracted corn oil (63). The graph also shows that about 7.5% of feedstock by weight of extracted corn oil (63) can be achieved at an extractant to feedstock ratio of about 10:1 and that about 7.8% of feedstock by weight of extracted corn oil (63) can be achieved at an extractant to feedstock ratio of about 20:1.

EXAMPLE 2

As a second non-limiting example of the endosperm corn oil extraction system (65), 22.37 grams of an amount of the extracted endosperm stream (61) (also referred to as the feedstock) providing a −24 wire+40 wire particle size (particles fell through a 24 wire screen but were retained by a 40 wire screen) was introduced into an extraction vessel and extracted with an amount of carbon dioxide for 40 minutes at a pressure of about 9000 pounds per square inch at a temperature of 80° C. at a flow rate of 6 liters per minute (the "extraction event").

Figure 10:
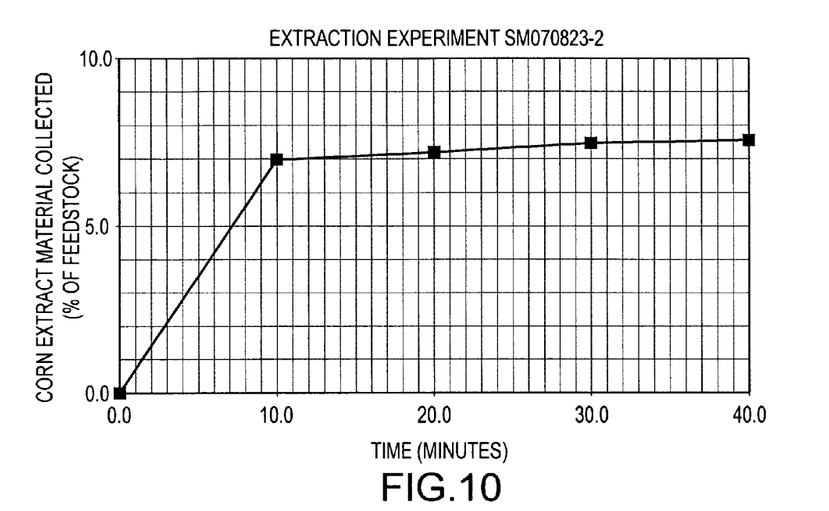
FIG. 10 provides a graph which plots the amount of corn oil extracted as a weight percent of the amount of an extracted corn endosperm stream against the duration of time.

Now referring to FIG. 10, which shows a graph of the results of the extraction event as the amount of corn oil (63) (or corn endosperm extraction material collected reported as a percent weight of the feedstock) over the 40 minute duration of the extraction event. A total amount of 1.8 grams of corn oil (63) was extracted (7.8% of feedstock by weight of feedstock). As can be understood from the graph shown in FIG. 8, substantially all the corn oil (63) extractable from the amount of the extracted endosperm stream (61) (feedstock) can be obtained with the first ten minute interval of the extraction event.

Figure 11:
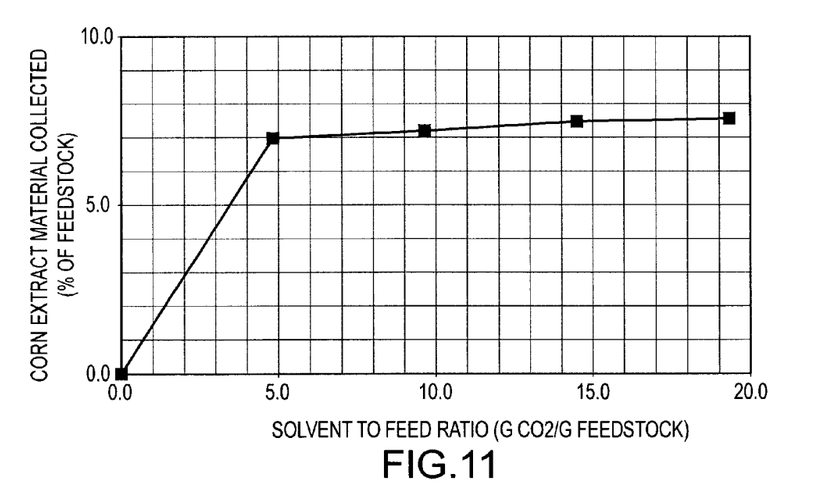
FIG. 11 provides a graph which plots the amount of corn oil extracted as a weight percent of the amount of an extracted corn endosperm stream against the extractant to feedstock ratio.

Now referring to FIG. 11 which shows a graph of the results of the amount of corn oil (63) (or corn endosperm extraction material collected reported as a percent weight of the feedstock) over the amount of carbon dioxide utilized per gram of the feedstock, it can be understood that lesser and greater extraction efficiencies can be determined for a particular set of extraction conditions and reported as an extractan to feedstock ratio. For example, for extraction conditions utilizing and amount of carbon dioxide at 9000 psi at about 80° C. a comparably greater efficiency extraction can be achieved at about 4.5:1 to about 5.5:1 extractant to feedstock ratio to produce about 7% of feedstock by weight of extracted corn oil (63). The graph also shows that about 7.2% of feedstock by weight of extracted corn oil (63) can be achieved at an extractant to feedstock ratio of about 10:1 and that about 7.8% of feedstock by weight of extracted corn oil (63) can be achieved at an extractant to feedstock ratio of about 20:1.

As can be understood, the results achieved utilizing the extraction conditions of EXAMPLE 1 and EXAMPLE 2 are substantially similar when performing the extraction event at 9000 psi even though the temperature between the extraction events was conducted at dissimilar temperatures of about 80° C. and about 110° C. respectively. While efficiency of other extraction conditions may be of a lesser or greater degree of efficiency than provided by the EXAMPLES, the EXAMPLES are not intended to be limiting, but rather intended to allow the person of ordinary skill in the art to practice a broad range of extraction conditions encompassed by the invention at pressures of between about 7,500 psi and about 10,000 psi and at temperatures of between about 70° C. and about 110° C. in various permutations and combinations depending on the application.

As can be easily understood from the foregoing, the basic concepts of the present invention may be embodied in a variety of ways which includes the best mode of the invention. The invention involves numerous and varied corn fractionation and corn oil extraction devices and methods of corn fractionation and extracting corn oil in various permutations and combinations thereof. While certain examples are provided in the context of dry corn fractionation processes, it is not intended that these examples limit the use of the invention to corn germ derived solely from these inventive dry corn fractionation process (17), but rather are intended to be illustrative such that a person of ordinary skill in the art can make and use the invention in the context of the numerous and varied processes that produce an amount of corn germ from which corn germ oil (23) can be extracted.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "mill" should be understood to encompass disclosure of the act of "milling"—whether explicitly discussed or not—and, conversely, were there effectively disclosure of the act of "milling", such a disclosure should be understood to encompass disclosure of a "mill" and even a "means for milling." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the dry corn fractionation devices or systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method of kernel fractionation, comprising:
   a) fracturing a plurality of corn kernels to generate a plurality of corn particles, wherein said plurality of corn particles comprise a dry mixture of a plurality of corn bran particles, a plurality of corn germ particles, and a plurality of corn endosperm particles;
   b) fractionating said dry mixture of said plurality of corn bran particles, said plurality of corn germ particles, and said plurality of corn endosperm particles into a corn germ fraction, a corn endosperm fraction, and a corn bran fraction;
   c) separating said corn endosperm fraction into a first endosperm stream and a second endosperm stream, said first endosperm stream a non-extracted endosperm stream;
   d) establishing an amount of said second endosperm stream inside a corn endosperm extraction zone;
   d) fluidicly engaging an amount of extractant to said amount of said second endosperm stream inside said extraction zone;
   e) extracting an amount of corn oil from said amount of said second endosperm stream fluidicly engaged by said amount of extractant to produce an extracted endosperm stream; and
   f) generating an amount of endosperm-germ cake from said extracted endosperm stream containing a reduced amount of corn oil.

2. The method of kernel fractionation of claim 1, further comprising the step of combining said amount of endosperm-germ cake with said non-extracted endosperm stream.

3. The method of kernel fractionation of claim 2, further comprising the step of introducing a combination of said amount of endosperm-germ cake and said non-extracted endosperm stream into an ethanol production process.

4. The method of kernel fractionation of claim 3, further comprising the step of removing an amount of non-extractable endosperm particles from said extracted endosperm stream.

5. The method of kernel fractionation of claim 4, further comprising the step of combining said amount of non-extractable endosperm particles from said extracted endosperm stream to said non-extracted endosperm stream.

6. The method of kernel fractionation of claim 1, wherein said step of fluidicly engaging an amount of extractant to said amount of said second endosperm stream inside said extraction zone comprises the step of fluidicly engaging an amount of supercritical carbon dioxide to said amount of said second endosperm stream inside said extraction zone, and wherein said step of extracting an amount of corn oil from said amount of said second endosperm stream fluidicly engaged by said amount of extractant comprises the step of extracting an amount of corn oil from said amount of said second endosperm stream fluidicly engaged by said amount of supercritical carbon dioxide.

7. The method of kernel fractionation of claim 6, wherein said amount of supercritical carbon dioxide has a pressure of between about 7,500 psi and about 10,000 psi and a temperature of between about 70° C. and 110° C. to said amount of said second endosperm stream inside said extraction zone.

8. The method of kernel fractionation of claim 6, wherein said amount of supercritical carbon dioxide has a pressure of between about 8,500 psi and about 9,500 psi and a temperature of between about 80° C. and 110° C. to said amount of said second endosperm stream inside said extraction zone.

9. The method of kernel fractionation of claim 6, wherein said amount of supercritical carbon dioxide having has a pressure of about 9,000 psi and a temperature of between about 80° C. and 110° C. to said amount of said second endosperm stream inside said extraction zone.

10. The method of kernel fractionation of claim 9, further comprising the step of adjusting said amount of supercritical carbon dioxide to said amount of second endosperm stream to a ratio of between about 4.5:1 to about 20:1.

11. The method of kernel fractionation of claim 10, wherein said step of adjusting said amount of supercritical carbon dioxide to said amount of second endosperm stream to a ratio of between about 4.5:1 to about 20:1 comprises the step of adjusting said amount of supercritical carbon dioxide to said amount of second endosperm stream to a ratio of between about 4.5:1 to about 10:1.

12. The method of kernel fractionation of claim 10, wherein said step of adjusting said amount of supercritical carbon dioxide to said amount of second endosperm stream to a ratio of between about 4.5:1 to about 10:1 comprises the step of adjusting said amount of supercritical carbon dioxide to said amount of second endosperm stream to a ratio of between about 4.5:1 to about 5.5:1.

* * * * *